United States Patent [19]

Rinehart

[11] 4,282,168
[45] Aug. 4, 1981

[54] S-(SUBSTITUTED PHENYL) N-ALKYL THIOLCARBAMATES

[75] Inventor: Jay K. Rinehart, Akron, Ohio

[73] Assignee: PPG Industries, Inc., Pittsburgh, Pa.

[21] Appl. No.: 843,014

[22] Filed: Oct. 17, 1977

Related U.S. Application Data

[62] Division of Ser. No. 702,563, Jul. 6, 1976, Pat. No. 4,055,657.

[51] Int. Cl.$^3$ ............................................. C07C 155/02
[52] U.S. Cl. ................................................. 260/455 A
[58] Field of Search ..................................... 260/455 A

[56] References Cited

U.S. PATENT DOCUMENTS

| | | | |
|---|---|---|---|
| 2,977,209 | 3/1961 | Tilles et al. | 71/100 |
| 3,046,189 | 7/1962 | Jacobi et al. | 260/455 A |
| 3,265,563 | 8/1966 | Tilles et al. | 424/300 |
| 3,301,885 | 1/1967 | Richter et al. | 260/455 A |
| 3,687,653 | 8/1972 | Bollinger et al. | 260/455 A |
| 3,781,440 | 12/1973 | Marco et al. | 260/455 A |
| 3,932,632 | 1/1976 | Adolphi et al. | 260/455 A |

FOREIGN PATENT DOCUMENTS

789575  7/1968  Canada ............................ 260/455 A
6606753 11/1966 Netherlands ..................... 260/455 A

OTHER PUBLICATIONS

T. M. Velega, *Journal of American Chemical Society*, 31, pp. 1150–1153, (1965).
R. Reimschneider et al., Monstsch, 84, 518 (1953).
D. G. Crosby et al., Journal of Amer. Chem. Society, 76, 4458, (1954).
M. S. Newman et al., Journal of Organic Chemistry, 31, 3980–3983, (1961).
Chem. Abs., 69 (1968), 86600e.

*Primary Examiner*—Henry R. Jiles
*Attorney, Agent, or Firm*—Edward J. Whitfield; Robert J. Grassi

[57] ABSTRACT

Both novel and known S-(substituted-phenyl) N-alkylthiolcarbamates such as 4-fluorophenyl N-methylthiolcarbamate, and S-(substituted-phenyl) N,N-dialkylthiolcarbamates such as 2-chlorophenyl N,N-dimethylthiolcarbamate are disclosed. These are useful to control plant pests such as *Phytophthorans infestans* (Late Blight of Tomatoes) and *Pythium ultimum* (Damping Off). Also disclosed are the methods of controlling this plant pest with these compounds.

4 Claims, No Drawings

S-(SUBSTITUTED PHENYL) N-ALKYL THIOLCARBAMATES

This is a division of application Ser. No. 702,563, filed July 6, 1976, now U.S. Pat. No. 4,055,657.

BACKGROUND OF THE INVENTION

This invention concerns S-(substituted-phenyl) N-alkylthiolcarbamates and S-(substituted-phenyl) N,N-dialkylthiolcarbamates, particularly those in which the alkyl is from one to four carbon atoms, and their control of plant pests such as *Phytophthorans infestans* and *Pythium ultimum*.

DESCRIPTION OF THE PRIOR ART

Plant pests such as fungi of *Phytophthorans infestans* and *Pythium ultimum*, continually affect the growth of crops, trees, and other desirable vegetation. One method of controlling plant pests such as fungi is by application of chemicals which affect the fungi. These chemicals are applied to the soil, to the desirable plant, or directly to the fungi itself. Because thousands of species of fungi exist, which differ in tolerance to chemicals, new chemicals must be discovered which are effective to control the deleterious effects of particular fungi.

The prior art shows that certain thiolcarbamates are effective against plant pests. The following patents and references illustrate the different thiolcarbamates claimed to be effective against certain plant pests.

U.S. Pat. Nos. 2,977,209 and 3,265,563 disclose S-phenyl N-alkylthiolcarbamates, S-chlorophenyl N-alkylthiolcarbamates, S-ethoxyphenyl N-allylthiolcarbamate, S-ethoxyphenyl N-alkylthiolcarbamates, S-p-tolyl N-alkylthiolcarbamates, and S-2,4-dimethylphenyl N-alkylthiolcarbamates as herbicides and fungicides. U.S. Pat. No. 3,632,332 discloses S-4-methylbenzyl-N,N-diethylthiocarbamate as a herbicide for rice fields. U.S. Pat. No. 3,301,885 discloses S-substituted phenyl N-alkyl, N-alkoxythiolcarbamates as herbicides, miticides, and insecticides. U.S. Pat. No. 3,687,653 discloses trifluoromethylbenzyl N-alkylthiolcarbamates as herbicides. U.S. Pat. No. 3,046,189 and Canadian Pat. No. 789,575 discloses S-alkyl N-alkylthiocarbamates as nematocides. R. Reimschneider and O. Lorenz, in *Monstsch.*, 84, 518 (1953) describe S-phenyl N,N-dimethylthiolcarbamate, and D. G. Crosby and C. Niemann, *Journal of American Chemical Society*, 76, 4458 (1954) describe S-phenyl N-cyclohexylthiolcarbamate, and S-phenyl N-phenylthiolcarbamate. Netherlands Patent No. 6,606,753 discloses S-phenyl N-trifluoromethylphenylthiocarbamate and S-substituted phenyl N-substituted trifluoromethylphenylthiocarbamates as anthelmintics. M. S. Newman and H. A. Karnes, *Journal of Organic Chemistry*, 31, pages 3980–3983 describe S-β-naphthyl N,N-dimethylthiolcarbamate, S-2-nitrophenyl N,N-dimethylthiolcarbamate, S-3-nitrophenyl N,N-dimethylthiolcarbamate, S-2,4,5-trichlorophenyl N,N-dimethylthiolcarbamate, S-3-trifluoromethylphenyl N,N-dimethylthiolcarbamate, S-2,3,5,6-tetramethylpentyl N,N-dimethylthiolcarbamate, S-4-tertbutylphenyl N,N-dimethylthiolcarbamate, S-2-methoxyphenyl N,N-dimethylthiolcarbamate, and S-4-methoxyphenyl N,N-dimethylthiolcarbamate. U.S. Pat. No. 3,932,632 discloses insecticides of dithiophosphate compounds mixed with S-aryl N,N-dialkylthiolcarbamates, or S-aryl N,N-dialkylenethiolcarbamates, or S-aryl N,N-dialkynylthiolcarbamates, or S-aryl N,N-(alkyl, alkylene, or alkynyl), (alkyl, alkylene, or alkynyl)thiolcarbamates where the aryl may be a substituted phenyl.

SUMMARY OF THE INVENTION

This invention concerns both novel and known substituted phenylthiolcarbamates of the general formula:

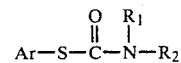

wherein:

Ar is 4-nitrophenyl, 4-bromophenyl, 4-fluorophenyl, 3,4-dibromophenyl, 3,4-dichlorophenyl, or 2-chlorophenyl;

$R_1$ is hydrogen, or an alkyl of from one to four carbon atoms;

$R_2$ is an alkyl of from one to four carbon atoms; and their use to control plant pests, such as *Phytophthorans infestans* and *Phythium ultimum*.

DESCRIPTION OF THE PREFERRED EMBODIMENTS

The S-(substituted-phenyl) N-alkylthiolcarbamates, and S-(substituted-phenyl) N,N-dialkylthiolcarbamates are represented by the general graphic formula:

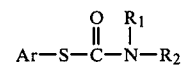

wherein:

Ar is a substituted phenyl of 4-nitrophenyl, 4-bromophenyl, 4-fluorophenyl, 3,4-dibromophenyl, 3,4-dichlorophenyl, and 2-chlorophenyl;

$R_1$ is hydrogen, or an alkyl of from one to four carbon atoms; and $R_2$ is an alkyl of from one to four carbon atoms.

The phrase "an alkyl of from one to four carbon atoms" as used herein and in the claims refers to: methyl, ethyl, n-propyl, isopropyl, n-butyl, sec-butyl, isobutyl, and tert-butyl.

Some specific compounds representative of the novel compounds in which Ar is any of the substituted phenyls mentioned herein, $R_1$ is hydrogen, and $R_2$ is an alkyl of from one to four carbon atoms mentioned herein are:

S-4-nitrophenyl N-methylthiolcarbamate;
S-4-bromophenyl N-ethylthiolcarbamate;
S-4-fluorophenyl N-n-propylthiolcarbamate;
S-3,4-dibromophenyl N-isopropylthiolcarbamate;
S-2-chlorophenyl N-n-butylthiolcarbamate;
S-4-nitrophenyl N-sec-butylthiolcarbamate;
S-4-bromophenyl N-isobutylthiolcarbamate;
S-4-fluorophenyl N-tert-butylthiolcarbamate; and
S-3,4-dichlorophenyl N-isopropylthiolcarbamate.

When Ar is any of the substituted phenyls mentioned herein, and $R_1$ is hydrogen, the preferred $R_2$ alkyl is methyl, ethyl, n-propyl, and isopropyl. Specific compounds representative of these preferred compounds are:

S-4-nitrophenyl N-ethylthiolcarbamate;
S-4-bromophenyl N-n-propylthiolcarbamate;
S-4-fluorophenyl N-isopropylthiolcarbamate;
S-3,4-dibromophenyl N-methylthiolcarbamate;
S-2-chlorophenyl N-ethylthiolcarbamate; and
S-3,4-dichlorophenyl N-n-propylthiolcarbamate.

When $R_1$ is hydrogen, those compounds are especially preferred in which Ar is any of the substituted phenyls mentioned herein, and $R_2$ is methyl. Specific compounds being:
S-4-nitrophenyl N-methylthiolcarbamate;
S-4-bromophenyl N-methylthiolcarbamate;
S-4-fluorophenyl N-methylthiolcarbamate;
S-3,4-dibromophenyl N-methylthiolcarbamate;
S-2-chlorophenyl N-methylthiolcarbamate; and
S-3,4-dichlorophenyl N-methylthiolcarbamate.

Some specific compounds representative of the compounds in which Ar is any of the substituted phenyls mentioned herein, and $R_1$ and $R_2$ are any of the alkyls mentioned herein are:
S-4-nitrophenyl N-methyl, N-tert-butylthiolcarbamate;
S-4-bromophenyl N-ethyl, N-isobutylthiolcarbamate;
S-4-fluorophenyl N-n-propyl, N-sec-butylthiolcarbamate;
S-3,4-dibromophenyl N-isopropyl N-butylthiolcarbamate;
S-2-chlorophenyl N-butyl N-methylthiolcarbamate; and
S-3,4-dichlorophenyl N,N-dibutylthiolcarbamate.

When $R_1$ and $R_2$ are alkyls, those compounds are preferred in which Ar is any of the substituted phenyls mentioned herein, $R_1$ is methyl, and $R_2$ is methyl, ethyl, n-propyl, or isopropyl. Specific compounds representative of these preferred compounds are:
S-4-nitrophenyl N-methyl, N-methylthiolcarbamate;
S-4-bromophenyl N-methyl, N-ethylthiolcarbamate;
S-4-fluorophenyl N-methyl, N-n-propylthiolcarbamate;
S-3,4-dibromophenyl N-methyl, N-isopropylthiolcarbamate;
S-3,4-dichlorophenyl N-methyl, N-isopropylthiolcarbamate; and
S-2-chlorophenyl N-methyl, N-propylthiolcarbamate.

Where $R_1$ and $R_2$ are alkyls, those compounds are highly preferred in which Ar is any of the substituted phenyls mentioned herein and both $R_1$ and $R_2$ are methyl. Specific compounds being:
S-4-nitrophenyl N,N-dimethylthiolcarbamate;
S-4-bromophenyl N,N-dimethylthiolcarbamate;
S-4-fluorophenyl N,N-dimethylthiolcarbamate;
S-3,4-dibromophenyl N,N-dimethylthiolcarbamate;
S-3,4-dichlorophenyl N,N-dimethylthiolcarbamate; and
S-2-chlorophenyl N,N-dimethylthiolcarbamate.

When $R_1$ is hydrogen or an alkyl, and $R_2$ is an alkyl, those compounds in which Ar is 4-nitrophenyl, or 3,4-dichlorophenyl are especially preferred. Some specific examples representative of these compounds are:
S-4-nitrophenyl N-n-butylthiolcarbamate;
S-3,4-dichlorophenyl N-isobutylthiolcarbamate;
S-4-nitrophenyl N-isopropylthiolcarbamate;
S-3,4-dichlorophenyl N-ethylthiolcarbamate;
S-4-nitrophenyl N-ethyl, N-butylthiolcarbamate; and
S-3,4-dichlorophenyl N-methyl N-ethylthiolcarbamate.

SYNTHESIS OF THE COMPOUNDS a. Synthesis Routes

The compounds may be synthesized by the following routes:
(1) Reaction of substituted phenylthiols of the general formula ArSH with the appropriate isocyanates of the general formula $R_2NCO$, wherein Ar and $R_2$ have the same significance as mentioned hereinbefore.
(2) Reaction of a substituted phenyl thiolchloroformate of the general formula

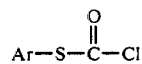

with an amine of the general formula

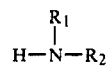

wherein Ar, $R_1$, and $R_2$ have the same significance as defined hereinbefore.
(3) Reaction of a substituted phenylthiol of the general formula ArSH with a carbamoyl chloride of the general formula

wherein Ar, $R_1$, and $R_2$ have the same significance as defined hereinbefore.

b. Synthesis by Reaction of Substituted Phenylthiol and an Isocyanate

The following examples illustrate the synthesis of compounds by reaction of a substituted phenylthiol with the appropriate isocyanate.

EXAMPLE I

S-4-fluorophenyl N-methylthiolcarbamate

Methyl isocyanate (2.4 grams, 42 millimoles) of anhydrous ethylether (10 milliliters) was slowly added (20 minutes) to a stirred mixture of 4-fluorobenzenethiol (5.2 grams, 40.5 millimoles) and triethylamine (one to two drops) in anhydrous ethylether (50 milliliters). The clear reaction mixture was refluxed for four hours, and the ethylether solvent was allowed to evaporate off.

A crystalline material (8.1 grams, >100 percent yield) was obtained, which was recrystallized from benzene (100 milliliters) to yield 6.6 grams of crystalline S-4-fluorophenyl N-methylthiolcarbamate. The crystalline material had a melting point of 105.5°–108° Centigrade, and an infrared spectrum with a N—H band at 3300 centimeters$^{-1}$ and a C=O band at 1650 centimeters$^{-1}$.

EXAMPLE II

S-4-bromophenyl N-methylthiolcarbamate

The procedure in Example I was followed using 7.6 grams (40 millimoles) of 4-bromobenzenethiol and 2.4 grams (42 millimoles) of methylisocyanate to obtain 12.6 grams (>100 percent yield) of a crude crystalline material. This was recrystallized from 100 milliliters of benzene to give 8.6 grams of crystalline S-4-bromophenyl N-methylthiolcarbamate with a melting point of 116°–120° Centigrade, and an infrared spectrum with a N—H band at 3260 centimeters$^{-1}$, and a C=O band at 1650 centimeters$^{-1}$.

Analysis for: $C_8H_8BrNOS$; Calculated: C, 39.04 percent; H, 3.27 percent; N, 5.69 percent; Found: C, 39.19, 39.30; H, 3.18, 3.13; N, 5.23, 5.38

EXAMPLE III

S-4-nitrophenyl N-methylthiolcarbamate

The procedure in Example I was followed using benzene solvent, 3.0 grams (52 millimoles) of methylisocyanate and 7.8 grams (50 millimoles) of 4-nitrobenzenethiol which was purified by a benzene azeotropic distillation. A crude crystalline product, 8.4 grams (79 percent yield) was obtained which was recrystallized from benzene to give 6.0 grams of crystalline S-4-nitrophenyl N-methylthiolcarbamate with a melting point of 135°–145° Centigrade and an infrared spectrum with a N—H band at 3320 centimeters$^{-1}$ and a C=O band at 1660 centimeters$^{-1}$.

Analysis for: $C_8H_8N_2O_3S$; Calculated: C, 45.27 percent; H, 3.80 percent, N, 13.20 percent; Found: C, 45.40, 45.39 percent; H, 3.64, 3.68 percent; N, 12.84, 12.89 percent

EXAMPLE IV

S-3,4-dichlorophenyl N-methylthiolcarbamate

The procedure of Example I was followed using 6.3 grams (35 millimoles) of 3,4-dichlorobenzenethiol and 2.1 grams (37 millimoles) of methylisocyanate to obtain 8.4 grams (100 percent yield) of a crude material. The material was recrystallized from benzene to give 6.5 grams of crystalline S-3,4-dichlorophenyl N-methylthiolcarbamate with a melting point of 130.5°–136° Centigrade and an infrared spectrum with a N—H band at 3280 centimeters$^{-1}$ and 1655 centimeters$^{-1}$.

Analysis for: $C_8H_7Cl_2NOS$; Calculated percentage: C, 40.69; H, 2.99; N, 5.93; Found percentage: C, 40.78, 41.04; H, 2.86, 2.85; N, 5.67, 5.70

Other inert solvents which dissolve the reactants and products and which are easily removed from the products by evaporation, drying, filtering, or washing, and which have a boiling point appropriate to the reaction temperature may be used in lieu of ethylether or benzene, such as tetrahydrofuran, hexane, and chloroform. The reaction temperature may vary from 0° C. to the boiling point of the refluxing mixture. Preferably the reaction temperature range is from 0° C. to 80° C.

c. Synthesis By Reaction of Substituted Phenylthiolchloroformates and Alkylamines The substituted phenylthiolchloroformates are formed from phosgene and the appropriate substituted phenylthiol. U.S. Pat. No. 3,165,544 describes one method of synthesizing these thiolchloroformates.

The following procedure is used to synthesize the compounds disclosed herein, particularly the S-substituted phenyl N,N-dialkylthiolcarbamates by the reaction of the appropriate thiolchloroformate and alkylamine.

A solution containing a substituted phenylthiolchloroformate of the general formula

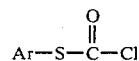

mentioned herein (45 millimoles) e.g., (3,4-dibromobenzenethiolchloroformate) in about 10 milliliters of ethylether is slowy added dropwise over a 20 minute period to a vigorously stirred amine solution. The amine solution contains about 100 milliliters of water, 100 milliliters of ethylether, 45 millimoles of triethylamine and about 45 millimoles of an alkylamine of the general formula

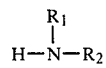

mentioned herein, (e.g.) diethylamine.

The reaction mixture is stirred for an additional half hour at ambient temperature, and the layers of solution are separated. The aqueous layer is washed once with about 100 milliliters of ethylether, and this ethylether washing and the ethylether layer of the solution are combined. The combined layers are washed with about 100 milliliters of aqueous solutions of 10 weight percent sodium hydroxide, and 10 weight percent hydrochloric acid, respectively, and then dried with anhydrous sodium sulfate ($Na_2SO_4$).

After filtering off the sodium sulfate, the ethylether solvent is removed by evaporation, and the impure S-substituted phenyl N-alkylthiolcarbamate or S-substituted phenyl N,N-dialkylthiolcarbamate, e.g., S-3,4-dibromophenyl N,N-diethylthiolcarbamate remaining is recrystallized from an inert solvent such as benzene.

d. Synthesis By Reaction of Substituted Phenylthiols With the Appropriate Carbamoyl Chloride The following procedure illustrates synthesis of the compounds particularly the S-substituted phenyl N,N-dialkylthiolcarbamates mentioned herein, by reaction of substituted phenylthiols of the general formula ArSH mentioned herein with the appropriate alkylcarbamoyl chloride of the general formula

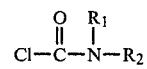

mentioned herein.

A five (5) milliliter anhydrous ethylether solution of fifty (50) millimoles of the appropriate alkylcarbamoyl chloride, e.g., dimethylcarbamoyl chloride and a five (5) milliliter anhydrous ethylether solution of fifty (50) millimoles of triethylamine are simultaneously added over a forty (40) minute period at ambient temperature to a stirred forty (40) milliliter anhydrous ethylether solution of fifty (50) millimoles of substituted phenylthiol (e.g., 2-chlorobenzenethiol). The reaction mixture is stirred and refluxed for about two (2) to two and one-half (2½) hours, and is cooled to room temperature and poured into about 50 milliliters of distilled water.

The organic layer and aqueous layer are separated from each other. The aqueous layer is extracted with ethylether and the extracts are combined with the organic layer, which is then washed with about one hundred (100) milliliters of a 10 weight percent aqueous solution of sodium hydroxide, and then washed with about one hundred (100) milliliters of a 10 weight percent aqueous solution of hydrochloric acid, respectively, and then dried with sodium sulfate which is then filtered off.

The solvent of ethylether is removed by evaporation, and the impure S-substituted phenyl N-alkylthiolcarbamate or S-substituted phenyl N,N-dialkylthiolcarbamate (e.g., S-2-chlorophenyl N,N-dimethylthiolcarbamate) is purified by recrystallization or other techniques if necessary.

PROPERTIES

The compounds disclosed herein are useful to control the deleterious effects of the fungus *Phytophthorans infestans,* and some are useful to also control the deleterious effects of the fungus *Pythium ultimum.*

These useful properties are illustrated by the following tests.

CONTROL OF LATE BLIGHT OF TOMATOES
(*Phytophthorans infestans*)

Test Procedure

This disease is caused by the fungus *Phytophthora infestans. The test procedure determines protectant properties of a compound; that is, whether the compound prevents plants from the effects of the disease, if the plants are contacted with the compound prior to exposure to the causal fungus.*

In this test, Bonny Best tomato plants, approximately five to six weeks old in five leaf growth stage grown under natural sunlight in a glass covered greenhouse are mounted on a compound turntable and sprayed to incipient run off at 40 pounds pressure for 60 seconds, equivalent to 50 gallons per acre, using solid cone, T-Jet 8001-E spray nozzle tip with a solution for dissolving the compound for testing is an acetone emulsion solution, containing 1995 ml. acetone, 4 ml. Span 85 ® (sorbitan trioleate), and 1 ml. Tween 80 ® (sorbitan monooleate polyalkylene derivative).

The pre-determined amount of test compound is dissolved in a volume of the stock solution equivalent to 19 percent by volume of the total spray volume using 90 percent by volume distilled water.

After the treated plants have dried, (4–8 hours), they are inoculated by uniformly spraying with a mixed sporangial and zoaspore suspension of the fungus *Phytophthora infestans,* taken directly from diseased plants, (50–70 plants per replicate), then incubated at 70° F. and 95 percent or more relative humidity. Inoculation consists of spraying at the rate of 100 milliliters of a suspension containing $10^6$ zoaspores and $10^5$ sporangia per 35 tomato plants. After an incubation period of about 40 hours (in the dark), which normally insures that the spores have a chance to infest the plants, the plants are placed in a glass greenhouse, using natural sunlight, and observed for signs of total infection lesions of the top three leaves visible to the naked eye (generally 3 to 5 days). The greenhouse operates at a temperature from 70° to 80° F. and a humidity range of from 50 to 90 percent.

The severity of the disease is determined by actual count of the developed lesions or inoculated but otherwise untreated controls. The test results are expressed as Control Effectiveness, which is determined by actual count of the number of developed lesions appearing on the respectively treated plants compared directly to equivalent developed lesions on inoculated but otherwise untreated controls. This control effectiveness is expressed as Percent Control which is calculated as follows:

$$\% \text{ control} = 100\% - 100\% \frac{\text{(number of lesions for all treated plants)}}{\text{(number of lesions for all control plants)}}$$

The foliar fungicidal test results are given in Table 1. Column 1 of Table 1 gives the Example number; column 2 lists the test compound, which is prepared according to the synthesis given herein unless indicated otherwise; column 3 gives the percent control obtained at 1,000 parts per million (ppm).

TABLE 1

| Example No. | Compound Applied | Percent Control of Late Blight of Tomatoes |
|---|---|---|
| V | S-β-naphthyl N,N-dimethyl-thiolcarbamate[d] | 51 |
| VI | S-phenyl N-methylthiolcarbamate[a] | 0 |
| VII | S-phenyl N,N-dimethylthiolcarbamate[a] | 0 |
| VIII | S-4-chlorophenyl N-methyl-thiolcarbamate[a,b] | 0[c] |
| IX | S-4-bromophenyl N-methyl-thiolcarbamate | 60 |
| X | S-4-nitrophenyl N-methyl-thiolcarbamate | 59 |
| XI | S-4-fluorophenyl N-methyl-thiolcarbamate | 67 |
| XII | S-3,4-dichlorophenyl N-methylthiolcarbamate | 72 |

[a] known compound described in U.S. Pat. No. 2,977,209.
[b] known compound described in U.S. Pat. No. 2,977,209 and U.S. Pat. No. 3,265,563.
[c] "Zero" (0) percent control at 500 ppm and lower concentrations.
[d] known compound - Journal of Organic Chemistry, 31, pages 3980–3983.

CONTROL OF *Pythium ultimum* (Damping Off)

TEST PROCEDURE

Oospores suspensions of *Pythium ultimum,* which have been examined with a haemocytometer for oospore (plus chlamydospore) numbers per milliliter, were blended at the rate of 1000 oospores per gram of dry sterilized soil.

A blend of sterile soil and the test compound (normally added to the soil as a solution) was also made. The chemically treated soil was mixed with the Pythium-inoculated soil and thoroughly mixed in a soil blender, and the mixture was equally divided, and division was placed into a container seeded with sugar beet seeds, water sealed, and placed in a greenhouse, maintained at 50–75 percent humidity, and 70°–80° Fahrenheit, for 2 weeks.

Containers of sterile soil only, sterile soil plus the test compound, and sterile soil plus *Pythium inoculum,* were also seeded with sugar beet seeds and placed in the greenhouse.

Observations were made for 14 days, and the final observation was made on the 14th day after preparing the samples.

Disease severity was determined by comparing the actual count of the surviving plants in Pythium-inoculated soil with the actual count of the surviving plants in sterile soil.

Control effectiveness of the test compound was determined by comparing the actual count of surviving plants in the chemically treated soil with the actual count of surviving plants in the Pythium-inoculated soil.

Each test consisted of at least three replicates.

The control effectiveness is expressed as percent control calculated by the following formula:

$$\% \text{ control} = 100\% \frac{\text{(total number of surviving plants in treated soil)}}{\text{(total number of surviving plants in untreated soil)}}$$

The amount of test chemical applied is expressed as pounds per acre (lb/A) for 6 inch depth of soil.

The test results for the compounds are shown in Table 2. Column 1 of the table gives the example number; column 2 gives the test compound which was synthesized as disclosed herein unless indicated otherwise; column 3 gives the percent control obtained at fifty (50) pounds per acre.

TABLE 2

PERCENT CONTROL OF *Pythium ultimum*

| Example No. | Compound Applied | Percent Control of *Pythium ultimum* |
|---|---|---|
| XIII | S-phenyl N-methylthiolcarbamate[a] | 0 |
| XIV | S-phenyl N-n-ethylthiolcarbamate[a] | 0 |
| XV | S-4-chlorophenyl N-methylthiolcarbamate[a] | 0 |
| XVI | S-4-bromophenyl N-methylthiolcarbamate | 0 |
| XVII | S-4-fluorophenyl N-methylthiolcarbamate | 47 |
| XVIII | S-4-nitrophenyl N-methylthiolcarbamate | 100<br>81[d]<br>71[e]<br>0[f] |
| XIX | S-3,4-dichlorophenyl N-methylthiolcarbamate | 67<br>81[b]<br>61[c]<br>0[d] |
| XX | S-phenyl N,N-dimethylthiolcarbamate[b] | 0 |
| XXI | S-β-naphthyl N,N-dimethylthiolcarbamate[c] | 0 |

[a] described in U.S. Pat. No. 2,977,209 and U.S. Pat. No. 3,265,563
[b] described in U.S. Pat. No. 2,977,209.
[c] described in Journal of Organic Chemistry, 31, pages 3980–3983.
[d] Percent control at 25 pounds per acre.
[e] Percent control at 12 pounds per acre.
[f] Percent control at 6 pounds per acre.

APPLICATION a. Suitable Agricultural Formulations

The compounds disclosed herein may themselves be applied directly to the area where the deleterious effects of the plant pests are to be controlled. It is, however, preferable to use suitable agricultural formulations which contain other ingredients which enhance application of the compound. These agricultural formulations will generally comprise about 5 percent to 95 percent or more by weight of one or more S-substituted phenyl N-alkyl or N,N-dialkylthiolcarbamate, of the general formula:

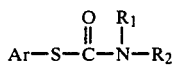

disclosed herein, or mixtures of these compounds, and either from 1 percent to 95 percent by weight of an agricultural diluent, or from 1 percent to 20 percent by weight of a surface active agent and other ingredients required to produce wettable powders, dusts, solutions, emulsifiable concentrates, granules, and the like, or both.

Wettable powders will contain from 25 to 80 percent active ingredients, from 0.1 percent to 5.0 percent wetters and dispersants with the balance consisting of inorganic absorptive diluents.

Since some compounds are solids, others are liquids, and others are viscous materials, they may be dissolved in one or more solvents and then sprayed upon the absorptive diluents of attapulgite clay, synthetic fine silica, and synthetic calcium and sodium alumino-silicates, or other solid insecticides, or foliar fungicides mentioned herein and then the solvent or solvents are evaporated off.

Emulsifiable oils will contain from 20 percent to 97 percent active ingredient, from 3.0 to 10.0 percent of an emulsifying agent, and may also contain from 1 percent to 77 percent water-immiscible solvent such as xylene or alkylated naphthalene.

Granules will contain from 5 percent to 25 percent active ingredient, and may also contain from 1 percent to 20 percent of a surfactant extended upon a granular base such as vermiculite or granular attapulgite. Granules produced by extrusion or tumbling will contain like amounts of active ingredient and surfactant.

b. Combinations With Other Insecticides and Fungicides

For the control of a wider range of crop-pests and diseases it is sometimes desirable to combine one or more of the thiolcarbamates of the general formula:

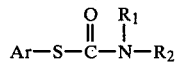

with from 0.05 to 4 parts by weight of insecticides and fungicides, etc., known to be effective against crop-pests and diseases in concentrated premix or during the application step for foliar applications. Examples of other pesticides are: granules containing stable metal azide-metal salt formulations disclosed in assignee's copending application entitled AZIDE-METAL SALT FORMULATIONS, Ser. No. 624,357, filed Oct. 21, 1975, containing S-4-methoxyphenyl N-2,3-dibromopropylthiolcarbamate, disclosed in assignee's copending application entitled S-p-METHOXYPHENYL N-BIS-2,3-DIBROMOPROPYLTHIOLCARBAMATE, Ser. No. 631,751, filed Nov. 7, 1975, or S-4-methoxyphenyl N,N-bis(2,3-dibromopropyl)thiolcarbamate disclosed in assignee's copending application entitled S-p-METHOXYPHENYL N,N-DIALLYLTHIOLCARBAMATE and S-p-METHOXYPHENYL N,N-BIS(2,3-DIBROMOPROPYL)THIOLCARBAMATE, Ser. No. 631,802, filed Nov. 7, 1975, Sevin 1(naphthyl-N-methylcarbamate), Chlorobenzilate (ethyl 4,4'-dichlorobenzilate), Guthion (O,O-diethyl-S-[4-oxo-1,2,3-benzotriazin-3(4H)-ylmethyl]phosphorodithioate), Disyston (O,O-diethyl-S-[2-(ethylsulfinyl)ethyl]phosphorodithioate), Maneb (manganous ethylene bisdithiocarbamate), Karathane (mixture of 2,4-dinitro-6-octylphenylcrotonate, 2,6-dinitro-4-octylphenylcrotonate, nitrooctylphenols (principally dinitro), 4-(1-methylheptyl)2,6-dinitrophenylcrotonate, 4-(1-ethylhexyl)2,6-dinitrophenylcrotonate, 4-(1-propylpentyl)-2,6-dinitrophenylcrotonate, 6-(1-methylheptyl)-2,4-dinitrophenylcrotonate, 6-(1-ethylhexyl)2,4-dinitrophenylcrotonate, and 6-(1-propylpentyl)2,4-dinitrophenylcrotonate), Blasticidin (blasticidin-S-benzylaminobenzenesulfonate), Benlate (methyl 1-(butylcarbamoyl)-2-benzimidazolecarbamate), or Plantvax (5,6-dihydro-2-methyl-1,4-oxathiin-3-carboxanilide-4,4-dioxide).

In some instances it is also desirable to include special purpose additives which will inhibit corrosion, reduce foaming, reduce caking, or increase flocculation.

The following example illustrates a suitable emulsifiable concentrate formulation, for dilution in water for spraying plants, particularly, plant foliage or for application to other plant parts as herein mentioned. In this emulsifiable concentrate formulation, the percentages are weight percent.

EXAMPLE XXII

Emulsifiable Concentrate Formulations

| | |
|---|---|
| 3,4-dichlorophenyl N-methylthiolcarbamate | 13% |
| Xylene | 41% |
| Isophorone | 41% |
| Atlox ® 3404* | 1% |
| Atlox ® 3403 F* | 4% |

*Commercial emulsifier for agricultural pesticides manufactured by Atlas Powder Co., Wilmington, Delaware, and registered with the U.S. Food and Drug Administration.

c. Amount of the Compounds Described Herein to Apply

The novel compounds described herein when used for a fungicide, to control Late Blight of Tomatoes (*Phytophthorans infestans*), are applied in an amount effective to control this plant test. This amount is a fungicidal amount, which amount will vary with the season of the year, the weather, and the severity of the disease. These fungus plant pests include those specifically described and shown herein as well as equivalent species which are biologically related such as those of the genus Phytophthorans and may be controlled by application of the compounds.

A single compound may be used in the formulation described herein, preferably a plurality of the compounds are used together either in a formulation or by concurrent application, that is applying one or more of the compounds to the plant itself. In other applications, one or more compounds may be applied to the plant, and within about 10 days, the one or more of same compounds, or different compounds may be applied to the plant so as to effectively control plant pests.

When the compounds of the general formula

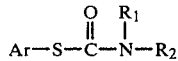

are applied as a foliar fungicide, the rate of application is from 20 parts per million to the amount tolerated by plant, generally from 500 to 10,000 parts per million (ppm) of one or more of the active compounds, applied as a solution to the point of run off, or as a powder or dust which thinly coats the plant part desired to be covered.

Those compounds in which $R_1$ is hydrogen and $R_2$ is methyl, ethyl, n-propyl, and isopropyl may be applied at lower rates of from 500 to 7500 ppm (parts per million). Those in which $R_2$ is methyl may be applied at still lower rates from 500 to 2000 ppm.

Those compounds in which $R_1$ and $R_2$ are an alkyl mentioned herein, are applied at rates from 500 to 9000 ppm. Those compounds in which $R_1$ is methyl and $R_2$ is methyl, ethyl, n-propyl, or isopropyl may be applied at lower rates of from 500 to 4000 ppm. Those compounds in which $R_1$ and $R_2$ are methyl are generally used at lower rates of from 500 to 2000 ppm.

When used to control the soil fungus *Pythium ultimum* the novel compounds may be applied at rates of from 6 pounds per acre per 6 inch depth of soil to as high as 500 pounds per acre per 6 inch depth of soil, depending upon, the application method, e.g., soil incorporation, discing, band, the type of formulation used, the plant species to be protected, the extend of the soil infestation, local conditions such as temperature, humidity, moisture content of the soil, nature of the soil, e.g., clay, loam, sand, pH, etc.

Those compounds in which Ar is 4-nitrophenyl, 4-fluorophenyl, 3,4-dichlorophenyl may be used at lower rates such as from 6 pounds per acre to 300 pounds per acre, of these compounds those in which $R_1$ and $R_2$ are methyl may be used at lower rates of 12 pounds per acre to 200 pounds per acre, and those in which $R_1$ is hydrogen and $R_2$ is methyl are generally used at the lowest rates of 12 pounds per acre to 50 pounds per acre. Preferably the compound is applied prior to planting the plants.

The phrase "to effectively control the deleterious effects of plant pest" as used herein and in the claims means that control required to increase the yield of plants growing in infested areas and treated with the compound, as compared to non-treated plants. This effective control may range from 10 percent to 100 percent control.

The phrase "applying an effective amount" as used herein and in the claims means applying that amount necessary to attain effective control by any application technique in which the compound and plant pest are brought into mutual contact, such as to the foliage of the plant, to the soil itself, to the fungus itself, or other plant pest.

d. Application To Control Other Plant Pests

Although the novel compounds of the general formula

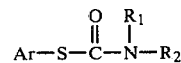

are used to control Late Blight of Tomatoes, this does not preclude their use against other plant pests. For example the compound 2-chlorophenyl N-methylthiolcarbamate may be used for systemic control of the deleterious effects of *Meloidogyne nemas* species such as *Meloidogyne incognita, Meloidogyne exigua* (Coffee Root-knot Nematode), *Meloidogyne arenaria* (Peanut Root-knot Nematode), *Meloidogyne hapla* (Northern Root-knot Nematode), and Citrus root Nematode.

Other species of nematodes may be controlled by applications other than systemic foliage contact, for example, by supplying the compounds having activity against the harmful effects of nematodes to the soil, by dipping the bulbs in solutions. Some examples of these other nematodes are:

| | |
|---|---|
| Aphelenchoides species | Bud and Leaf Nematodes |
| *Anguina tritici* | Wheat Nematode |
| *Anguina agrostis* | Grass Nematode |
| Belonolaimus species | Sting Nematodes |
| Criconemoides species | Ring Nematodes |
| *Ditylonchus dipsaci* | Stem and Bulb Nematode |
| *Ditylonchus Potato Rot Nematode* | |
| *Ditylonchus angustus* | Rice Nematode |
| *Dolichodorus heterocephalus* | Awl Nematode |
| Helicotylenchus species | Spiral Nematodes |
| *Heterodera rostochiensis* | Golden Nematode |
| *Heterodera tabacum* | Tobacco Cyst Nematode |
| *Heterodera schachtii* | Sugar Beet Nematode |
| *Heterodera carotae* | Carrot Root Nematode |
| *Heterodera gottingiana* | Pea Root Nematode |

| Heterdoera Soybean Cyst Nematode | |
|---|---|
| Hoplolaimus species | Lance Nematodes |
| *Pratylenchus brachyurus* | Smooth-headed Lesion Nematode |
| Pratylenchus species | Meadow Nematodes |
| *Pratylenchus musicola* | Banana Nematode |
| *Pratylenchus zeae* | Corn Nematode |
| *Radopholus similis* | Burrowing Nematode |
| *Rotylenchus reniformis* | Kidney-shaped Nematode |
| Trichodorus species | Stubby-root Nematodes |
| *Tylenchlorhynchus claytoni* | Tobacco Stunt Nematode |
| Xiphinema species | Dagger Nematodes |

Those compounds in which Ar is 4-nitrophenyl, $R_1$ is H, and $R_2$ is an alkyl mentioned herein, can be used at rates from 50 to 500 pounds per acre per 6 inch depth of soil to control the fungus *Sclerotium rolfsii*.

Those compounds in which Ar is 4-nitrophenyl or 4-fluorophenyl and $R_1$ is H and $R_2$ is an alkyl mentioned herein could be used at rates from 50 to 500 pounds per acre per 6 inch depth of soil to control the plant pest *Fusarium solani*, at rates from 2000 ppm to 10,000 ppm to control foliar fungus such as *Fusarium oxysporium* f. *lycopersici* which causes Fusarium Wilt of Tomatoes.

The compound of 4-bromophenyl N-methylthiolcarbamate could be used to control the foliar fungus *Piricularia oryzoe*, the cause of Rice Blast Disease.

While the invention has been described with reference to specific details of certain illustrative embodiments, it is not intended that it shall be limited thereby except insofar as such details appear in the accompanying claims.

I claim:
1. S-3,4-dichlorophenyl N-methylthiolcarbamate.
2. S-4-fluorophenyl N-methylthiolcarbamate.
3. S-3,4-dibromophenyl N-methylthiolcarbamate.
4. S-2-Chlorophenyl N-methylthiolcarbamate.

* * * * *